US00PP33779P2

(12) United States Plant Patent
Heuger

(10) Patent No.: US PP33,779 P2
(45) Date of Patent: Dec. 21, 2021

(54) ***HELLEBORUS* PLANT NAMED 'COSEH 6500'**

(50) Latin Name: ***Helleborus* x *ballardiae* X *Helleborus* x *hybridus***
Varietal Denomination: COSEH 6500

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 191 days.

(21) Appl. No.: 16/873,638

(22) Filed: May 27, 2020

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 5/00; A01H 6/72
See application file for complete search history.

*Primary Examiner* — June Hwu
(74) *Attorney, Agent, or Firm* — C. Anne Whealy

(57) ABSTRACT

A new and distinct cultivar of *Helleborus* plant named 'COSEH 6500', characterized by its upright to slightly outwardly spreading and mounded plant habit; moderately vigorous to vigorous growth habit; dark green-colored leaves; freely flowering habit; light yellow green-colored flowers with greyed purple to greyed red-colored margins and venation; and good garden performance.

2 Drawing Sheets

Figure 1:
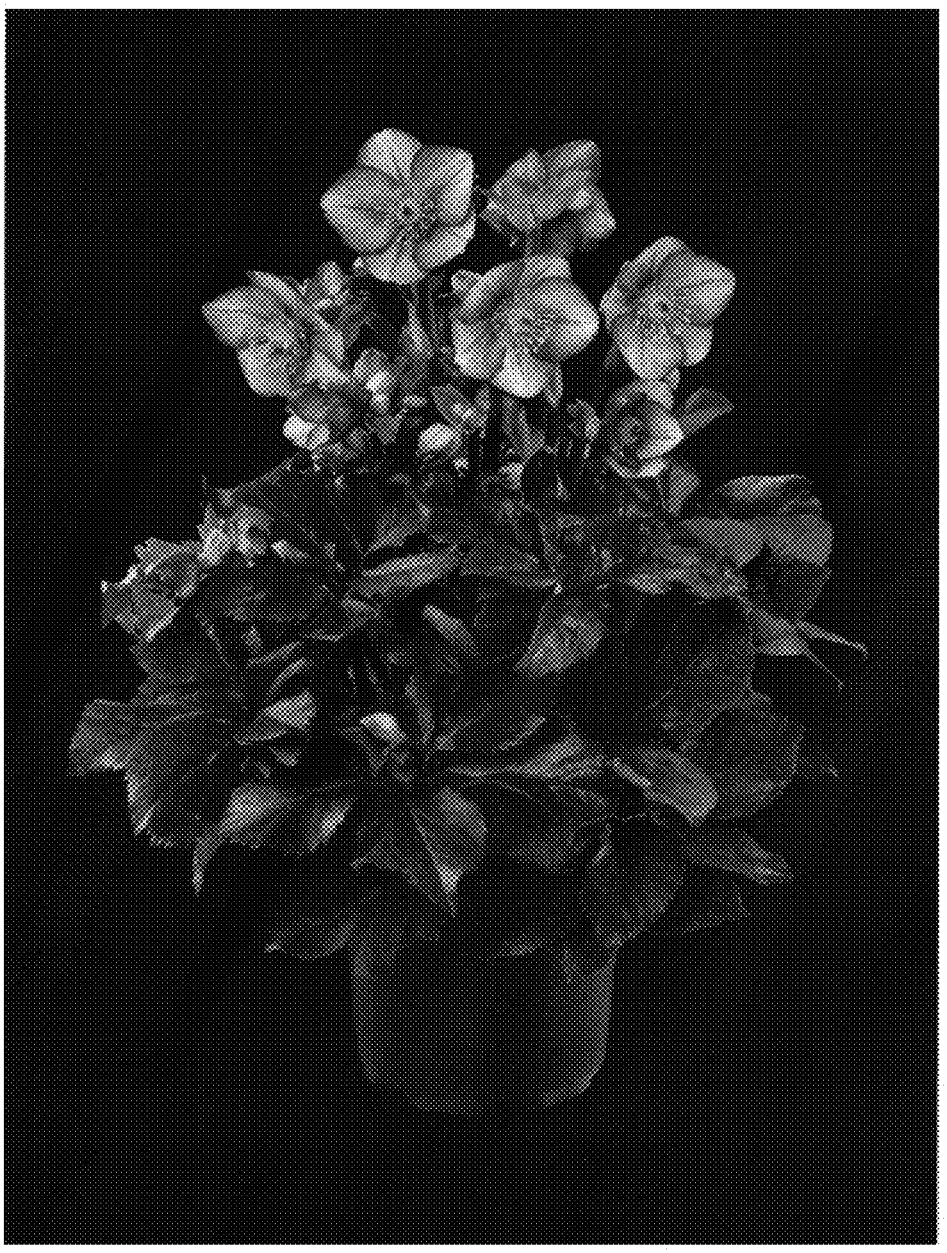

Botanical designation: *Helleborus* x *ballardiae* X *Helleborus* x *hybridus*.

Cultivar denomination: 'COSEH 6500'.

CROSS-REFERENCED TO CLOSELY-RELATED APPLICATIONS

Title: *Helleborus* Plant Named 'COSEH 6400'
Inventor/Applicant: Josef Heuger
Filed: Concurrently with the instant application (U.S. Plant patent application Ser. No. 16/873,645)
Title: *Helleborus* Plant Named 'COSEH 6600'
Inventor/Applicant: Josef Heuger
Filed: Concurrently with the instant application (U.S. Plant patent application Ser. No. 16/873,637)

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1388. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x

*ballardiae* X *Helleborus* x *hybridus* and hereinafter referred to by the name 'COSEH 6500'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2012 of a proprietary selection of *Helleborus* x *ballardiae* identified as code number P839, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2014.

Asexual reproduction of the new *Helleborus* plant by in vitro axillary meristem culture in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 6500'. These characteristics in combination distinguish 'COSEH 6500' as a new and distinct *Helleborus* plant:

1. Upright to slightly outwardly spreading and mounded plant habit.

2. Moderately vigorous to vigorous growth habit.
3. Dark green-colored leaves.
4. Freely flowering habit.
5. Light yellow green-colored flowers with greyed purple to greyed red-colored margins and venation.
6. Good garden performance.

Plants of the new *Helleborus* differ from plants of the female parent selection in the following characteristics:

1. Plants of the new *Helleborus* are more vigorous than plants of the female parent selection.
2. Plants of the new *Helleborus* flower later than plants of the female parent selection.

Plants of the new *Helleborus* differ from plants of the male parent selection in the following characteristics:

1. Plants of the new *Helleborus* are more vigorous than plants of the male parent selection.
2. Leaves of plants of the new *Helleborus* are darker green in color than leaves of plants of the male parent selection.

Plants of the new *Helleborus* can be compared to plants of *Helleborus* x *ballardiae* X *Helleborus* x *hybridus* 'COSEH 6400', disclosed in a U.S. Plant Patent application filed concurrently. Plants of the new *Helleborus* differ primarily from plants of 'COSEH 6400' in plant and growth habit as plants of the new *Helleborus* are shorter and broader than and not as vigorous as plants of 'COSEH 6400'.

Plants of the new *Helleborus* can be compared to plants of *Helleborus* x *ballardiae* X *Helleborus* x *hybridus* 'COSEH 6600', disclosed in a U.S. Plant Patent application filed concurrently. Plants of the new *Helleborus* differ primarily from plants of 'COSEH 6600' in flower color as plants of the new *Helleborus* have light yellow green-colored flowers with greyed purple to greyed red-colored margins whereas plants of 'COSEH 6600' have greyed purple to greyed red-colored flowers. In addition, plants of the new *Helleborus* are taller and broader than plants of 'COSEH 6600'.

Plants of the new *Helleborus* can also be compared to plants of *Helleborus* x *hybridus* 'ABCRD01' (U.S. Plant Pat. No. 24,149) also known as trade name 'Penny's Pink'. In side-by-side comparisons, plants of the new *Helleborus* differ primarily from plants of 'Penny's Pink' in the following characteristics:

1. Plants of the new *Helleborus* have dark green-colored leaves without distinct venation whereas plants of 'Penny's Pink' have green-colored leaves with distinct venation.
2. Plants of the new *Helleborus* differ from plants of 'Penny's Pink' in flower color as plants of the new *Helleborus* have light yellow green-colored flowers with greyed purple to greyed red-colored margins whereas plants of 'Penny's Pink' have greyed purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 6500' grown in a container.

Figure 2:
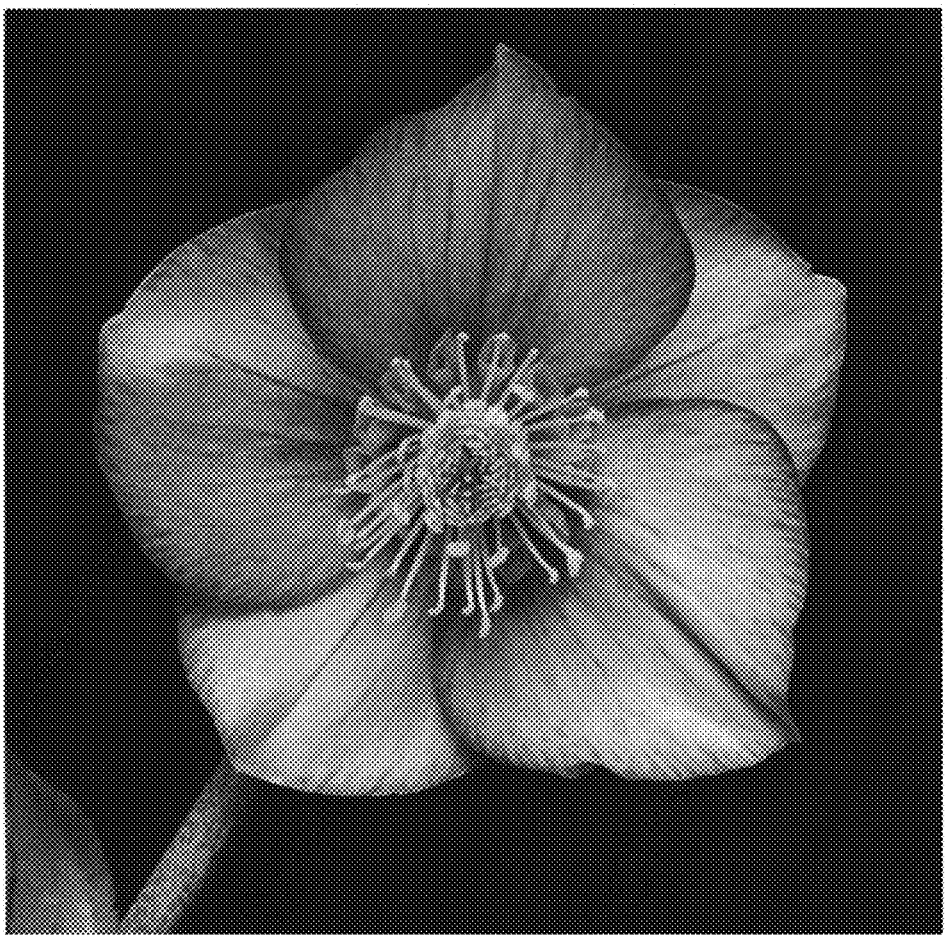

The photograph on the second sheet (FIG. 2 of 2) is a close-up view of a typical flower of 'COSEH 6500'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ballardiae* X *Helleborus* x *hybridus* 'COSEH 6500'.

Parentage:

*Female, or seed, parent*.—Proprietary selection of *Helleborus* x *ballardiae* disclosed as code number P839, not patented.

*Male, or pollen, parent*.—Unnamed selection of *Helleborus* x *hybridus*, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to slightly outwardly spreading and mounding plant habit with flowers held within and above the foliar plane; plant shape, roughly flattened globular; moderately vigorous to vigorous growth habit and rapid growth rate.

*Plant height, soil level to top of foliar plane*.—About 29 cm.

*Plant height, soil level to top of flowers*.—About 50.8 cm.

*Plant diameter* (*area of spread*).—About 76 cm.

Leaf description:

*Arrangement*.—Leaves arranged in a basal rosette; leaves palmately compound with typically five leaflets per leaf.

*Leaf length*.—About 20.8 cm.

*Leaf width*.—About 20.4 cm.

*Leaflet length*.—About 12.6 cm.

*Leaflet width*.—About 7.2 cm.

*Leaf shape*.—Palmate; orbicular in outline.

*Leaflet shape*.—Elliptic to ovate.

*Leaflet apex*.—Acute to bluntly acute.

*Leaflet base*.—Attenuate.

*Leaflet margin*.—Serrate; coarsely undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to NN137A; midvein tinged at the base with close to 184A. Developing leaflets, lower surface: Close to 148A; midvein, close to 183A. Fully developed leaflets, upper surface: Darker than between 139A and 147A; venation, close to 144A and at the base, tinged with close to 187A. Fully developed leaflets, lower surface: Close to 147B; venation, close to 183A.

*Petioles*.—Length: About 19.7 cm. Diameter: About 5.5 mm to 7 mm. Strength: Strong. Texture and luster, upper and lower surfaces: Smooth, glabrous; slightly glossy. Color, upper and lower surfaces: Close to 146D moderately covered with fine dots, close to 183B and proximally, more heavily covered and fine dots, close to 183A.

Flower description:

*Flower shape and habit*.—Rotate flowers; flowers moderately cupped; arranged in panicles; freely flowering habit with about six flowers per inflorescence and about 54 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 1.4 cm. Diameter: About 1 cm. Shape: Broadly ovate to oblong. Texture and luster: Smooth, glabrous; matte. Color: Close to 145C.

*Inflorescence height* (*including peduncle*).—About 55.2 cm.

*Inflorescence diameter*.—About 16.2 cm.

*Flower diameter*.—About 6.2 cm by 6.2 cm.

*Flower depth* (*height*).—About 2.4 cm.

*Petals*.—All petals are transformed into nectaries.

*Sepals*.—Quantity and arrangement: About five, arranged in a single whorl. Length: About 3.6 cm. Width: About 3.2 cm. Shape: Broadly ovate to broadly rhomboidal, slightly concave. Apex: Obtuse. Base: Truncate to broadly cuneate. Margin: Entire; not undulate to slightly undulate. Texture and luster, upper surface: Smooth, glabrous; matte. Texture and luster, lower surface: Smooth, glabrous; slightly glossy. Color: When opening, upper surface: Close to 157A; towards the margins and apex, close to 186C. When opening, lower surface: Close to 145D; towards the margins, close to 60B to 60C. Fully opened, upper surface: Close to 145C; towards the margins and apex, close to 186C; venation, close to 186C; with development, color becoming closer to 146D and towards the margins and apex, moderately tinged with close to 182B; venation, close to 187D. Fully opened, lower surface: Close to 145C; towards the margins and apex, strongly tinged with close to 60C to 60D; venation, similar to lamina; with development, color becoming closer to N148B to N148C, towards the margins and apex, strongly tinged with close to 183B and venation, close to 187B.

*Flower bracts*.—Quantity per flower: Typically one or two. Length: About 5.2 cm. Width: About 2.9 cm. Shape: Ovate. Apex: Tri-lobed. Base: Truncate. Margin: Sparsely and finely serrate; slightly undulate. Color, upper surface: Close to NN137A; venation, similar to lamina. Color, lower surface: Close to 147B; venation, close to 183A.

*Peduncles*.—Length: About 48.3 cm. Diameter: About 9 mm. Aspect: About 20° from vertical. Strength: Strong. Texture and luster: Smooth, glabrous; moderately glossy. Color: Close to 145C, heavily covered with fine dots, close to 182A and 182B.

*Pedicels*.—Length: About 2.2 cm. Diameter: About 2 mm. Aspect: About 10° to 25° from peduncle axis. Strength: Moderately strong. Texture and luster: Smooth, glabrous; moderately glossy. Color: Close to 145A, sparsely covered with fine dots, close to 182B to 182D.

*Reproductive organs*.—Stamens: Quantity per flower: About 80. Filament length: About 1.4 cm. Filament color: Close to NN155A. Anther shape: Double and broadly reniform; basifixed. Anther size: About 2 mm by 3 mm. Anther color: Close to 150C. Pollen amount: Moderate. Pollen color: Close to 4D to lighter than 4D. Pistils: Quantity per flower: About five to seven. Pistil length: About 1.2 cm. Stigma diameter: About 0.3 mm. Stigma shape: Club-shaped. Stigma color: Close to 157A. Style length: About 1.1 cm. Style color: Close to 185D. Ovary color: Close to 145C. Nectaries (transformed petals): Quantity per flower: About twelve. Length: About 1.3 cm. Diameter: About 4 mm. Shape: Tubular, flattened. Texture and luster, inner and outer surfaces: Smooth, glabrous; slightly glossy. Color, immature, inner surface: Close to 145B; towards the base, close to 145A. Color, immature, outer surface: Close to 145B; towards the base, close to 145A; basal spot, close to 146D. Color, mature, inner surface: Close to N144B; towards the apex, close to between 150B and 151D; venation, similar to lamina; with development, becoming closer to N144A and towards the apex, close to 151D. Color, mature, outer surface: Close to N144B; towards the apex, close to between 150B and 151D; basal spot, close to 152D; venation, similar to lamina; with development, becoming closer to N144A, towards the apex, close to 151D and basal spot, close to 152D.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 6500' as illustrated and described.

* * * * *